United States Patent
Diehl

(10) Patent No.: US 6,821,401 B2
(45) Date of Patent: Nov. 23, 2004

(54) SENSOR FOR MEASURING THE CONCENTRATION OF A GAS COMPONENT IN A GAS MIXTURE

(75) Inventor: Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/295,279

(22) Filed: Nov. 15, 2002

(65) Prior Publication Data

US 2003/0116433 A1 Jun. 26, 2003

(30) Foreign Application Priority Data

Nov. 15, 2001 (DE) ......................................... 101 56 248

(51) Int. Cl.$^7$ ....................... G01N 27/409; G01N 27/41
(52) U.S. Cl. ....................... 204/424; 204/425; 204/429
(58) Field of Search ................................. 204/421–429

(56) References Cited

U.S. PATENT DOCUMENTS 4,231,733 A * 11/1980 Hickam et al.
5,391,284 A * 2/1995 Hotzel ......................... 204/425
6,306,271 B1 * 10/2001 Kato et al.

FOREIGN PATENT DOCUMENTS

DE 199 41 051 3/2001

OTHER PUBLICATIONS

Wiedemann et al., "Exhaust Gas Sensors", Automotive Electronics Handbook, Chapter 6, McGraw–Hill, 1995.

* cited by examiner

Primary Examiner—Kaj K. Olsen
(74) Attorney, Agent, or Firm—Kenyon & Kenyon

(57) ABSTRACT

A sensor is described for measuring the concentration of a gas component in a gas mixture, particularly a lambda probe for measuring the oxygen concentration in the exhaust gas of an internal combustion engine, having a solid electrolyte and having two electrodes separated by the solid electrolyte, of which an outer electrode is exposed to the gas mixture and an inner electrode is situated in a cavity separated from the gas mixture by a diffusion barrier. To achieve a broadband measuring of the air ratio $\lambda$ and a simplified construction compared to a known lambda broadband probe having a pump cell and a Nernst cell, the sensor is operated according to predefined criteria, alternately as lean operation probe according to the limiting current principle and as transition probe having a pumped reference.

11 Claims, 1 Drawing Sheet

SENSOR FOR MEASURING THE CONCENTRATION OF A GAS COMPONENT IN A GAS MIXTURE

FIELD OF THE INVENTION

The present invention relates to a sensor for measuring the concentration of a gas component in a gas mixture.

BACKGROUND INFORMATION

A known sensor for regulating the air/fuel ratio of combustion mixtures for internal combustion engines, which is known as a $\lambda=1$ probe or transition probe (Wiedemann, Hötzel, Neumann, Riegel and Weyl "Exhaust Gas Sensors, Automotive Electronics Handbook", Ronald Jurgen, Chapter 6, McGraw-Hill 1995, ISBN 0-07-033189-8), works according to the principle of the galvanic oxygen concentration cell or Nernst cell having a solid electrolyte. A ceramic made of zirconium dioxide stabilized by yttrium oxide acts as solid electrolyte impermeable to gas, and over a broad range it is an almost perfect conductor of oxygen ions. The solid electrolyte equipped with catalytically active platinum cermet electrodes separates the exhaust gas from the surrounding air. Because of the migration of oxygen ions from the inner electrode to the outer electrode, a corresponding electrical field builds up, and a voltage can be picked off at the electrodes which is a function of the partial pressure ratios of the oxygen concentration at the electrodes. This probe measures accurately only in a small range around the present air/fuel ratio in the exhaust gas corresponding to the stoichiometric air/fuel ratio, that is, at the air ratio $\lambda=1$, and therefore has to be in a position to put the gas mixture reaching it into thermodynamic equilibrium.

In a sensor likewise described in the above-named publication, used for regulating the air/fuel ratio of combustion mixtures for internal combustion engines, which is denoted as a limiting current probe, or a lean mixture probe operating on the limiting current principle, a constant pump voltage is applied to the electrodes mounted on the solid electrolyte made of zirconium dioxide, again, stabilized with yttrium oxide, whose higher potential is at the outer electrode, which thus forms the anode. On account of this pump voltage, oxygen ions are pumped from the cathode to the anode, i.e. from the inner to the outer electrode. Since the continued flowing of oxygen molecules from the exhaust gas into the cavity surrounding the inner electrode is hindered by a diffusion barrier, a current saturation, the so-called limiting current, is reached above a pump voltage threshold value. This limiting current is proportional to the oxygen concentration in the exhaust gas. The characteristic curve of this limiting current probe shows an approximately linear increase in the pump current having an air ratio A in lean operation exhaust gas ($\lambda>1$) and an abrupt increase when $\lambda=1$. This limiting current probe therefore delivers accurate measuring values only in lean operation exhaust gas, and is not especially suitable for rich operation exhaust gas, that is, exhaust gas having a lack of oxygen ($\lambda<1$).

A gas sensor suitable for measurements in the case of rich and lean exhaust gas of the internal combustion engine, denoted as a broadband lambda probe, and likewise described in the above-named publication or in German Published Patent Application No. 199 41 051, in addition to the outer and inner electrodes mounted on the solid electrolyte, also has a measuring electrode or Nernst electrode situated opposite in the cavity of the inner electrode and a reference electrode which is situated in a reference gas channel separated from the cavity by the solid electrolyte. Air from the surroundings is supplied to the reference gas channel as reference gas. The broadband lambda probe is thus composed of two cells, namely a pump cell having an outer and an inner electrode which, depending on the oxygen concentration in the exhaust gas, pump oxygen in or out of the cavity, so as, in there, to set $\lambda=1$, and a concentration cell or Nernst cell having a Nernst electrode and a reference electrode which is used as an indicator for the oxygen concentration in the cavity. Using an electrical circuit, the pump voltage at the electrodes of the pump cell is regulated in such a way that there is constantly an oxygen concentration corresponding to $\lambda=1$ in the cavity. With regard to measuring technique, the pump voltage present at the electrodes of the pump cell is selected so as to maintain a predetermined voltage value at the concentration cell. The pump current flowing between the electrodes of the pump cell is utilized as a measuring signal proportional to the oxygen concentration in the exhaust gas. This broadband probe delivers a single-valued, monotonically increasing measuring signal in a broad lambda range ($0.65<\lambda>$infinity).

SUMMARY OF THE INVENTION

The sensor according to the present invention has the advantage of a sufficiently broadband concentration measurement of the gas component, when used as an exhaust gas sensor, that is, a broadband $\lambda$ measurement, and this along with a simplified design compared to the known broadband probe, since the additional gas reference of the broadband probe, which has to be kept constant using operating electronics, is omitted. In consideration of the heater, which is advantageous also in the sensor according to the present invention, for improving the catalytic activity of the electrodes on the solid electrolyte, the number of electrical contacts is reduced to only four because of the omission of the reference electrode. The broadband properties of the sensor according to the present invention are achieved, not by the construction of the sensor element, as in the known broadband probe, but rather by a control electronic system which can be customized much more easily.

Compared to the known limiting current probe, the sensor according to the present invention, at equal construction of the sensor element as in the limiting current probe, has the advantage that it delivers a clear measuring signal, even in the lean operation range, that is at prevailing lack of concentration of the gas component with respect to the stoichiometric ratio, or when it is used as an exhaust gas sensor in rich operation exhaust gas, and it signals a lack in the concentration or a rich exhaust gas.

The sensor according to the present invention is not only able to be used for broadband measurement in an internal combustion engine preferably working in lean operation, but also offers the possibility of being able to be used exclusively as a lean operation probe according to the limiting current principle, or as a $\lambda=1$ Transition probe, without changes in the construction of the sensor element having to be undertaken.

According to one advantageous specific embodiment of the present invention, in the operating mode "lean operation probe", a constant pump voltage having a higher voltage potential at the outer electrode is applied to the electrodes, and the pump current is measured as the measurement for the gas component concentration, whereas in the operating mode "transition probe", for pumping of the reference to the electrodes, a constant current source is connected having an anodic current flowing from the inner electrode to the outer electrode, and the electrode voltage is measured as a measure for the gas component concentration. In this context, the measurement is advantageously made in each case after the expiration of a transient recovery time subsequent to a switching over in the operating mode, the transient recovery time, after the change between operating mode "transition probe" and operating mode "limiting current probe", being less in lean exhaust gas than in rich exhaust gas or gas mixture, since the pumped reference is supported by the limiting current.

According to one advantageous specific embodiment of the present invention, the switching of the operating mode is done by an electronic control system, which, with the aid of an electronic switch, optionally connects the outer electrode to the constant voltage source or to the constant current source, and, synchronously with this, injects the respective measuring output.

The gas sensor is preferably used as a lambda probe for measuring the oxygen concentration in the exhaust gas of an internal combustion engine.

DETAILED DESCRIPTION

Figure 1:
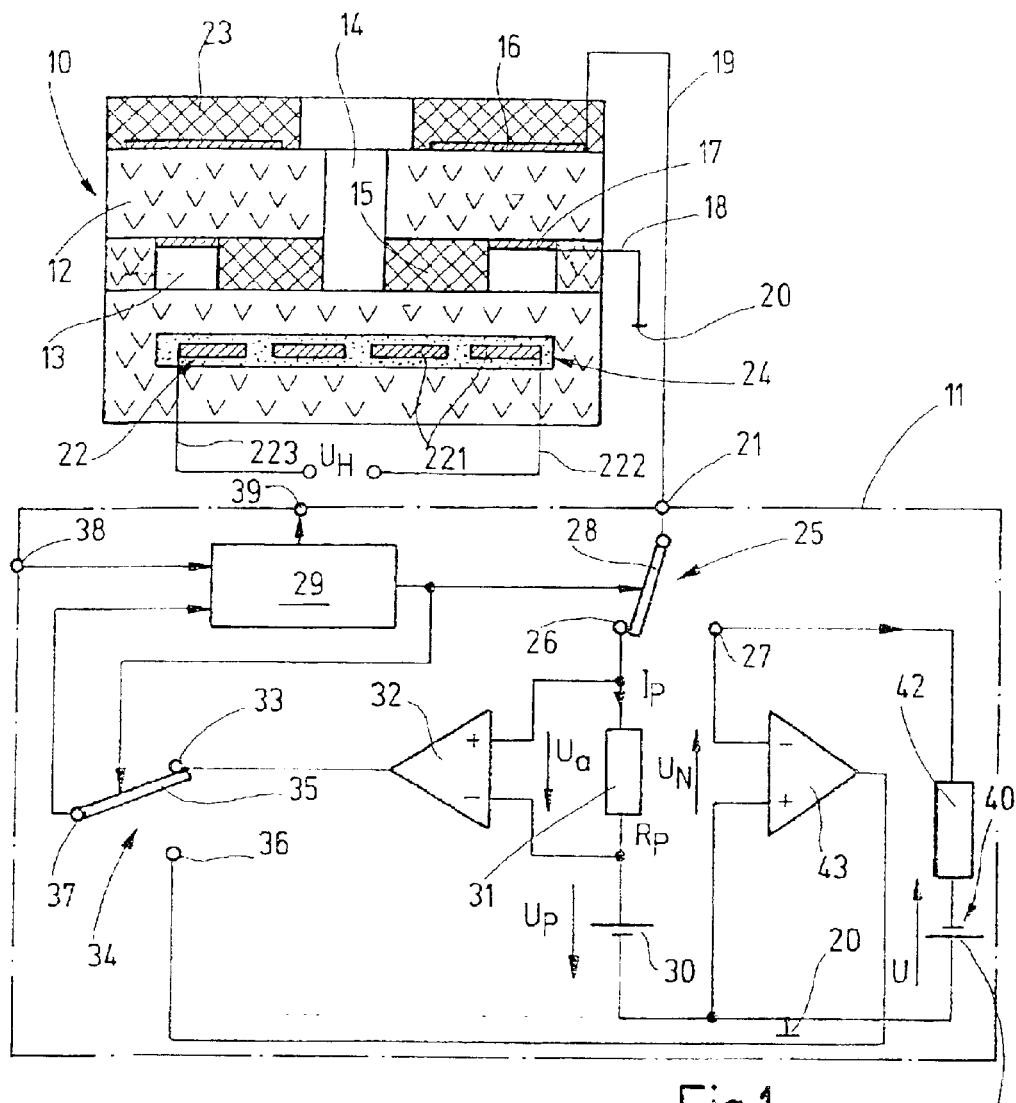
FIG. 1 shows a lambda probe for measuring oxygen concentration in the exhaust gas of an internal combustion engine.

The lambda probe shown schematically in FIG. 1, for measuring the oxygen concentration in the exhaust gas of an internal combustion engine, as the exemplary embodiment for a general sensor for measuring the concentration of a gas component in a gas mixture, is made up of a planar sensor element 10, exposed to the exhaust gas of the internal combustion engine or another gas mixture, and an electronic control system 11 for sensor element 10. Sensor element 10 has a solid electrolyte, for instance, a zirconium dioxide ceramic 12 stabilized with yttrium oxide, in which a cavity 13 is formed, which, for example, is ring-shaped. Cavity 13 is in contact with the exhaust gas via a central opening 14, which is inserted perpendicularly into $ZrO_2$ ceramic 12, and is covered from opening 14 by a porous diffusion barrier 15. On the upper side of $ZrO_2$ ceramic 12 there is a large-area outer electrode 16 covered by a porous protective layer 23, and within cavity 13 a preferably small-area inner electrode 17 is positioned on the side of the solid electrolyte facing away from outer electrode 16. In the exemplary embodiment, inner electrode 17 is circular in shape, and is connected to a zero potential 20 via a supply line 18, while the outer electrode 16, which is also ring-shaped and encloses central opening 14 is connected to a terminal 21 of electronic control system 11 via a supply line 19. Below cavity 13, a heater 22 is situated in $ZrO_2$ ceramic 12, which is embedded in an insulation 24 made of aluminum oxide ($Al_2O_3$), and is connected to a heating voltage UH via connecting lines 222, 223. Heater 22 is formed in meander shape, so that, in sensor element 10 shown in cross section in FIG. 1, the individual meander courses 221 of heater 22 may be seen in profile.

Electronic control circuit 11 has an electronic change-over switch 25, controlled by a control device 29, which is shown symbolically as a mechanical change-over switch 25 having a switching contact 28 that is able to be changed over between two connecting contacts 26, 27. At the one connecting contact 26 a series circuit is connected which is made up of a constant voltage source 30 delivering a pump voltage UP and of a measuring resistor 31, measuring resistor 31 lying between connecting contact 26 and the upper voltage potential of constant voltage source 30. The lower voltage potential of constant voltage source 30 is connected to zero potential 20. A measuring voltage $U_a$ picked off at measuring resistor 31 is supplied to a voltage amplifier 32, whose output is connected to a connecting contact 33 of a second electronic change-over switch 34, here again shown symbolically as a mechanical change-over switch 34, having a switching contact 35 and a further connecting contact 36, which is switched synchronously with first change-over switch 25 by control device 29. Output 37 of second change-over switch 34 is connected to control device 29. At its input side, control device 29 is also connected to a connecting clamp 38 of electronic control circuit 11, via which state variables characterizing the current operating condition of the internal combustion engine are supplied to control device 29.

At connecting contact 27 of change-over switch 25 a constant current source 40 is connected, which is made up of a voltage source 41 and a high-resistance resistor 42. In this context, resistor 42 is connected to connecting contact 27, and the upper voltage potential of voltage source 41 is connected to zero potential 20. A measuring voltage $U_N$, picked off between connecting contact 27 and zero potential 20 is supplied to a second voltage amplifier 43, whose output is connected to connecting contact 36 or second change-over switch 34. On account of the synchronous change-over of the two change-over switches 25 and 34, effected by control device 29, the lambda probe may be operated, on the one hand, as a lean operation probe according to the limiting current principle and, on the other hand, as transition probe having a pumped reference.

Figure 2:
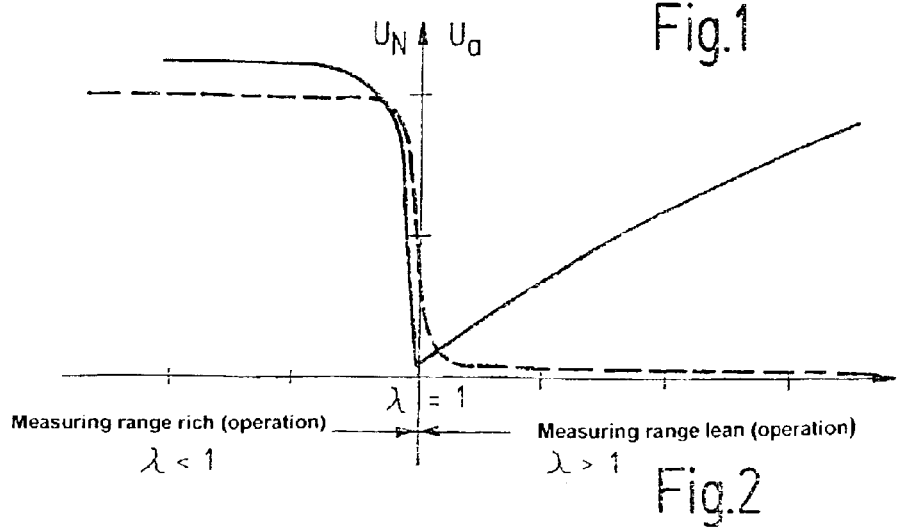
FIG. 2 shows a plot of the characteristic curve vs λ of the sensor according to FIG. 1.

In operating mode "lean operation probe", change-over switches 25 and 34 take up their positions as shown in FIG. 1. Outer electrode 16 is connected via measuring resistor 31 to the upper voltage potential of constant pump voltage $U_P$ of constant voltage source 30. Oxygen ions are pumped by inner electrode 17 to outer electrode 16, because of fixed pump voltage $U_P$ present between outer electrode 16 and inner electrode 17. Because of the continued flow of oxygen molecules from the exhaust gas, which is hindered by diffusion barrier 15, a limiting current or a pump current $I_P$ is established which is a measure of the oxygen concentration in the exhaust gas. This pump current $I_P$ is picked off as measuring voltage $U_a$ at measuring resistor 31, and, amplified by amplifier 32, is supplied to control device 29 via change-over switch 34. Control device 29 generates an actual value corresponding to the measuring voltage for the oxygen concentration in the exhaust gas, which may be picked off at a connecting clamp 39 of electronic control unit 11 for regulating the air/fuel ratio in the combustion mixture of the internal combustion engine. The lambda probe has a characteristic curve $U_a=f(\lambda)$ as shown in a solid line in FIG. 2, the air ratio lambda being plotted on the abscissa and the measuring voltage $U_a$, the measure for pump current $I_P$ being plotted on the ordinate.

If change-over switches 25, 34 are switched over, so that connecting clamp 21 os electronic control circuit 11 is connected to connecting contact 27 of first change-over switch 25 and connecting contact 37 of second change-over switch 34 is connected to connecting contact 36, then, due to the connection of constant current source 40 to electrodes 16, 17, outer electrode 16 becomes the cathode, and an anodic current flows from inner electrode 17 to outer electrode 16. As a result of this, oxygen ions are pumped from outer electrode 16 to inner electrode 17, and in cavity 13 an oxygen reference is built up. After a transient recovery time, a measuring voltage $U_N$ is obtained between electrodes 16, 17, whose magnitude is determined by the oxygen concentration in the exhaust gas. The lambda probe has a characteristic curve $U_N=f(\lambda)$ shown as a broken line in FIG. 2, the air ratio $\lambda$ being again plotted on the abscissa and the measuring voltage or Nernst voltage $U_N$ being plotted on the ordinate.

The change-over of change-over switches 25, 34 may take place in such a way that in operating mode "lean operation probe" that change-over switching to operating mode "transition probe" occurs at intervals for a short period of time, in order to detect whether a rich exhaust gas is present. In addition, in control device 29 a program is stored having state variables, of the internal combustion engine, among which of necessity a rich exhaust gas appears. As soon as such a state variable is reported to control device 29 via connecting clamp 38, control device 29 switches over the lambda probe into operating mode "transition probe" for the duration of the presence of this state variable. Measuring voltages $U_a$ and $U_N$ are each picked off only after the expiration of a transient recovery time that follows an operating mode changeover. In this connection, the transient recovery time in lean exhaust gas is lower than in rich exhaust gas, since the pumped reference is supported by the oxygen limiting current. Lean exhaust gas is also the prevailing operating state of this lambda probe.

In order to reduce the dead volume when the pumping direction is changed, that is, when switching over from operating mode "lean operation probe" to operating mode "transition probe" and vice versa, the volume of cavity 13 is designed to be as small as possible. In the extreme case, diffusion barrier 15 may fill cavity 13 completely if inner electrode 17 is small, that means that it may be directly mounted on inner electrode 17. Diffusion barrier 15 is designed for a low limiting current such as 0.5–3 mA, so that, in operating mode "transition probe having pumped reference", approximately the same current is required as that which appears as pump current in operating mode "limiting current probe". Outer electrode 16 is designed to be as large as possible in order to achieve a low inner resistance.

What is claimed is:

1. A sensor for measuring a concentration of a gas component in a gas mixture, comprising:
   a solid electrolyte conductive for ions;
   a diffusion barrier; and
   a plurality of electrodes separated by the solid electrolyte, an outer electrode of the plurality of electrodes being exposed to the gas mixture and an inner electrode of the plurality of electrodes being situated in a cavity separated from the gas mixture by the diffusion barrier, wherein:
   an operating mode is provided that is able to be switched over as a lean operation probe according to a limiting current principle and as a transition probe having a pumped reference, and wherein at least one of the following conditions is met:
   (a) in the operating mode corresponding to the lean operation probe, at the plurality of electrodes, a pump voltage, picked off from a constant voltage source and having a higher voltage potential than the inner electrode, is present at the outer electrode, and as a measure for the concentration of the gas component, a pump current caused by the pump voltage is measured after an expiration of a transient recovery time that follows a changeover switching of the operating mode, and
   (b) in the operating mode corresponding to the transition probe, for the purpose of pumping the reference at the plurality of electrodes, a constant current source is connected, having an anodic current flowing from the inner electrode to the outer electrode, and an electrode voltage is measured after the expiration of the transient recovery time that follows the changeover switching of the operating mode as a measure for the concentration of the gas component.

2. The sensor as recited in claim 1, wherein:
the cavity has a small volume, and
the inner electrode has a small area.

3. The sensor as recited in claim 2, wherein:
the cavity is completely filled up by a part of the diffusion barrier.

4. The sensor as recited in claim 1, wherein:
the outer electrode has a large area.

5. The sensor as recited in claim 1, further comprising:
a control device for switching over the operating mode.

6. The sensor as recited in claim 5, further comprising:
a change-over switch, wherein:
the control device controls the change-over switch to alternately connect the outer electrode to one of the constant voltage source and the constant current source.

7. The sensor as recited in claim 5, wherein:
the control device, during the operating mode corresponding to the lean operation probe, switches over at intervals, for a short period of time, to the operating mode corresponding to the transition probe.

8. The sensor as recited in claim 5, wherein:
in the control device a program is stored having state variables of a gas mixture generator, in which is present a lack of concentration of the gas component to be measured in the gas mixture, and during an appearance of the state variables the control device switches over to the operating mode corresponding to the transition probe.

9. The sensor as recited in claim 1, wherein:
the gas component includes oxygen,
the gas mixture includes an exhaust gas of an internal combustion engine, and
the sensor is used as a lambda probe for measuring an oxygen concentration in the exhaust gas of the internal combustion engine.

10. The sensor as recited in claim 1, wherein:
the solid electrolyte is impermeable to gas.

11. The sensor as recited in claim 1, further comprising:
a porous protective layer covering the outer electrode.

* * * * *